US006238284B1

(12) United States Patent
Dittgen et al.

(10) Patent No.: US 6,238,284 B1
(45) Date of Patent: May 29, 2001

(54) TRANSDERMAL COMPOSITIONS WITH ENHANCED SKIN PENETRATION PROPERTIES

(75) Inventors: Michael Dittgen, Apolda; Sabine Fricke; Christoph Völkel, both of Jena; Kathrin Ahrens, Reinheim; Hagen Gerecke, Jena, all of (DE); Kai Köpke, Triengen (CH)

(73) Assignees: Jenapharm GmbH & Co. KG; LTS Lohmann Therapie-Systeme AG, both of (DE)

( * ) Notice: Subject to any disclaimer, the term of this patent is extended or adjusted under 35 U.S.C. 154(b) by 0 days.

(21) Appl. No.: 09/341,416

(22) PCT Filed: Jan. 13, 1998

(86) PCT No.: PCT/DE98/00157

§ 371 Date: Sep. 10, 1999

§ 102(e) Date: Sep. 10, 1999

(87) PCT Pub. No.: WO98/30203

PCT Pub. Date: Jul. 16, 1998

(30) Foreign Application Priority Data

Jan. 13, 1997 (DE) .............................................. 197 01 949

(51) Int. Cl.$^7$ ...................................................... C09J 5/02
(52) U.S. Cl. ........................... 456/325; 156/327; 156/283; 424/443; 424/448
(58) Field of Search .................................... 424/448, 449, 424/443; 156/325

(56) References Cited

U.S. PATENT DOCUMENTS

| | | | |
|---|---|---|---|
| 4,379,454 | * 4/1983 | Campbell et al. | 604/897 |
| 4,637,930 | * 1/1987 | Konno et al. | 424/28 |
| 4,879,119 | * 11/1989 | Konno et al. | 424/449 |
| 5,422,361 | * 6/1995 | Munayyer et al. | 514/408 |
| 5,573,778 | * 11/1996 | Therriault et al. | 424/448 |
| 5,676,968 | * 10/1997 | Lipp et al. | 424/448 |

FOREIGN PATENT DOCUMENTS 44 02 462 A1    1/1994 (DE) .

OTHER PUBLICATIONS

B.W. Barry, "Lipid–Protein–Partitioning theory of skin penetration enhancement", Journal of Controlled Release, 15 (1991) 237–248.

R. Hüttnrauch, S. Fricke and P. Zielke; "The effect of water structure on the hydrogelling of polymethylmethacrylates. The ice theory of hydrogels", Pharmazie 40, H6 (1985).

Helmut Loth, "Skin Permeability", Method and Find. Exp. Clin Pharacol., 11(3), 155–164 (1989).

Hatanaka T., et al., "An Application of the Hydroeynamic Pore Theory to Percutaneous Absorption of Drugs", Pharm. Research, vol. 11; 1994 654–658.

Yamashita, F., et al., "In Vivo and in Vitro Analysis of Skin Penetration Enhancement Based on a Two–Layer Diffusion Model with Polar and Nonpolar Routes in the Stratum Corneum", Pharm Research, vol. 11, 1994 185–191.

Fartash, M., "The nature of the epidermal barrier: structural aspects", Advanced Drug Delivery Reviews 18 1996 273–282.

Ghosh, et al., "Methods of Enhancement of Transdermal Drug Delivery: Part I, Physical and Biochemical Approaches", Pharm Tech. 1993 72–96.

Ghosh, et al., "Methods of Enhancement of Transdermal Drug Delivery: Part IIA, Chemical Permeation Enhancers", Pharm. Tech. 1993 62–84.

* cited by examiner

Primary Examiner—Thurman K. Page
Assistant Examiner—Isis Ghali
(74) Attorney, Agent, or Firm—D. Peter Hochberg; Katherine R. Vieyra; William H. Holt

(57) ABSTRACT

The invention relates to a transdermal therapeutic system for application to the skin and/or mucosa consisting of at least one active substance in the form of a solid dispersion in combination with at least one destructuring agent and/or at least one structuring agent in a common matrix.

4 Claims, 2 Drawing Sheets

TRANSDERMAL COMPOSITIONS WITH ENHANCED SKIN PENETRATION PROPERTIES

This application is a 371 of PCT/DE98/00157 filed Jan. 13, 1998.

DESCRIPTION

The invention relates to a transdermal therapeutic system for application to the skin and/or mucosa consisting of at least one active substance in the form of a solid dispersion in combination with at least one destructuring agent and/or at least one structuring agent in a common matrix.

The invention thus relates to a method for improving the cutaneous permeation of active substances, which can be employed in particular for producing a transdermal therapeutic system (TTS) intended for application to the skin or mucosa.

The term "TTS" describes an administration device which adheres to the target organ which is the skin or mucosa and moreover allows the contained medicinal substance to exert systemic activity in the body by passing through the target organ.

The terms destructuring agent and structuring agent derive from the "ice" theory of hydrogels as described, for example, by Hüttenrauch et al. (Pharmazie 40, p. 427, 1985).

Compositions used for transdermal administration of active substances are known in a wide variety of forms:

U.S. Pat. No. 4,777,047 describes formulations for transdermal administration which contain a calcium channel blocker and surface-active auxiliaries such as isopropyl myristate or ethyl oleate in a solvent. The solvents generally mentioned are propylene glycol, linolenic acid, oleyl alcohol, Solketal or dimethyl sulphoxide.

U.S. Pat. No. 5,422,361 describes a cream or lotion which contains a lipophilic pharmaceutical active substance. The basic material used in this case is a physically and chemically stable oil-in-water emulsion which has a content of N-methyl-2-pyrrolidone, dimethyl sulphoxide, Solketal or oleyl alcohol. The basic materials described for Solketal and dimethyl sulphoxide have a maximum content of these substances of 10% by weight.

DE-C 43 09 830 describes an active substance plaster for delivering estradiol to the skin. The active substance plaster has an active substance reservoir consisting of a contact adhesive. A penetration accelerant, namely monoisopropylideneglycerol (MIPG, Solketal) or monoisopropylidenediglycerol (MIPD) is present in the polymer matrix of the contact adhesive to improve the bioavailability of estradiol.

Akhter, S. A. et al. (J. Pharm. Pharmacol. 36, Suppl., p. 7 (1984)) describe solutions of an active substance in the solvent Solketal to which 7% oleic acid is added as penetration-enhancing agent.

Dosage forms of these types for transdermal administration may be adequate for certain purposes, in particular for active substances for which the permeability of the skin is relatively good. However, as a rule, the epidermis, for example of humans, has relatively low permeability for active substances. Accordingly, on use of the known formulations, ordinarily too little active substance is transported through the skin into the bloodstream. In addition, cutaneous intolerance is common, such as, for example, skin irritation or even allergic effects. This is particularly true when steroid hormones are to be employed as active substances.

The preferred area of use of transdermal medicinal forms are symptoms, diseases, deficiency states and similar needs, such as nausea, heart/circulatory failure, hormone deficiency, the wish for contraception. These needs require provision of the active substance which is longer lasting, uniform or adapted to the biological rhythm of the blood level.

Typical TTSs release the contained medicinal substance uniformly over a prolonged period. However, additionally more complicated systems and mixed types (mixed systems) have also been described. Examples of TTSs mentioned by D'Mello (Transdermal Patch Drug Delivery, Scrip report BS750, PJB Publications Ltd., 1995) or in the "Rote Liste" (publisher: Bundesverband der pharmazeutischen Industrie (BPI), 1996) are:

Nicotine patches,
Hyoscine patch,
Glyceryl trinitrate patches,
NSAID patches,
Fentanyl patch,
Clonidine patch,
Oestradiol patch,
Oestradiol/Norethisterone patch,
Estradiol vaginal rings,
Isosorbide dinitrate ointments,
Isosorbide dinitrate transdermal sprays,
Glyceryl trinitrate ointments.

TTSs for insulin and other peptide active substances, including certain "releasing hormones", are being developed.

The production of the TTSs disclosed to date already in many cases takes account of the fact that not all active substances permeate through the skin to a sufficient extent. However, satisfactory functioning of the systems depends crucially on ensured permeation.

According to the recent review (Ghosh T. K., Banga, A. K., Pharm. Technol., 17 (March) 72–96 (1993) and 17 (April) 62–87 (1993)), there are physical, chemical and biological possibilities for improving cutaneous permeation. The use of so-called penetration promoters is to be regarded as a chemical possibility. These substances penetrate into the skin and interact with the constituents of the stratum corneum, which is the main impediment to penetration of the active substance. Penetration promoters reduce the resistance of the skin and thus increase the passage (flux) of the active substance through the skin. In most cases they also beneficially affect the active substance partition ratio between skin and vehicle (Franz, T. J., Tojo, K., Shah, K. R., Kydonieus, A., Transdermal Delivery, in Kydonieus, A. (Ed.) Treatise on Controlled Drug Delivery, Marcel Dekker, Inc., 341–422 (1992); Loth, H., Meth. and Find. Exp. Clin. Pharmacol., 11 (3), 155–164, (1989); Robson, D. L., Thesis, University of Bradford, Postgraduate School of Studies in Pharmacy, 1988, p. 1–25).

The transdermal flux takes place mainly intercellularly. This involves the permeating substance penetrating through the lipophilic cell structures (lipophilic route) so that penetration promoters which affect this route ought, depending on the region of the cell structure (cf. Fartasch, M. The nature of the epidermal barrier: Structural aspects. Advan. Drug Delivery Rev. 18(3), 273–282 (1996)), to have three sites of action (Barry, B. W., J. Controlled Release, 15, 237–248, (1991)), namely in the direct vicinity of polar head groups (region A)
in the aqueous region between the head groups (region B) and within the nonpolar constituents of the lipid bilayers (region C).

The site of action of most permeation promoters is known, but details are still lacking for some substances (Table 1).

TABLE 1

Classification of penetration promoters according to the site of action

| Site of action (predominant) | Penetration promoter |
|---|---|
| Region A | Water, dioxolane derivatives, ethyl acetate, urea*, ethanol and short-chain monohydric alcohols ($C_2$–$C_6$)*, propylene glycol* |
| Region B | Ethanol |
| Region C | DMSO*, DMF**, laurocapram and derivatives, fatty acids (e.g. oleic acid), surfactants (e.g. decyl methyl sulphoxide), terpenes |
| Unclear assignment | Isopropanol, glycerol, monohydric alcohols ($C_8$–$C_{14}$), alkanes, alkyl halides, amides, pyrrolidone derivatives, fatty acid esters, cyclodextrins, polyethylene glycols |

Additionally affects:
*keratin fibrils
**region A (solvation)

The overview in Table 1 makes it very clear that regions A and C are almost exclusively the sites of action of the well-known permeation promoters. These promoters aim at affecting either the head groups or the lipophilic chains. Only ethanol is thought to act in the aqueous region in the vicinity of the head groups. It can thus be said that the well-known permeation promoters, with the exception of ethanol, affect in particular the lipophilic regions and promote the lipophilic flux.

On the other hand, it is known that an alteration in the lipophilic regions is associated with serious impairments of the condition of the skin. These impairments extend from drying out and embrittlement to cracks, marked irritation, reddening, exzema and similar skin damage. This also applies to ethanol, the concentration of which is therefore limited on dermal application. In addition, ethanol has the disadvantage of ease of evaporation so that supersaturation states occur, the disadvantages of which will be explained later.

It is, however, known that the flux is possible by two routes, by the nonpolar route already mentioned and also by the pore diffusion route (polar route) (Yamashita, F., Bando, H., Koyama, Y., Kitagawa, S., Takakura, Y., Hashida, M., In Vivo and In Vitro Analysis of Skin Penetration Enhancement Based on a Two-layer Diffusion Model with Polar and Nonpolar Routes in the Stratum Corneum, Pharm. Res. 11, 185–191 (1994)).

The total of the two fluxes is obtained as in Equation 1:

$$J = J_L + J_P \quad \text{(Eq. 1)}$$

with J total flux, $J_L$ lipophilic flux, $J_P$ pore flux

The lipophilic flux.is generally predominant. The skin is therefore scarcely permeable, in particular to hydrophilic medicinal substances, especially since the proportion of area of the pores available for the pore flux, and the size of the pores (0.38–1.58 nm) are comparatively small.

To improve the pore flux, it has already been proposed (Hatanaka, T., Manabe, E., Sugibayashi, K., Morimoto, Y., An Application of the Hydrodynamic Pore Theory to Percutaneous Absorption of Drugs, Pharm. Res. 11, 654–658 (1994)), to use a solvent with high cutaneous permeability. The authors postulate that it is possible in this way to transfer active substances dissolved in the solvent through the skin. It emerged with the example of ANP and isosorbide dinitrate (ISDN) as active substance that the method fails with this medicinal substance which diffuses mainly by the lipophilic route.

The methods known to date for producing a transdermal medicinal form thus predominantly exhibit the considerable disadvantage that particular active substances with a certain degree of hydrophilicity, for example certain hormones, can be transported through the skin to an only inadequate extent. This fact is manifested, for example, by a testosterone plaster which must be applied to the scrotum if the hormone is to be absorbed transdermally to a sufficient extent. The proposed method for improving the pore flux with suitable solvents in the variant published by Hatanaka, T., Manabe, E., Sugibayashi, K., Morimoto, Y. appears promising, but only relatively low fluxes are achieved, and it has yet to be proved whether active substances in fact follow the solvent flux. In the case of ISDN, the method failed because the substance on its own permeates better through the skin by a factor of 10 than does the ANP employed as accelerant.

U.S. Pat. No. 4,379,454 describes a dependence of the active substance flux (estradiol) on the enhancer flux (ethanol). It was found in this case that an increased ethanol permeation rate likewise increases the estradiol permeation. However, there is a disadvantage in the potential of ethanol to irritate the layers of the skin on prolonged use.

It is therefore an object of the present invention to provide a TTS which overcomes the abovementioned disadvantages of the state of the art.

It is therefore an object of the invention to provide compositions for transdermal administration which are improved by comparison with known compositions, in particular in relation to the ability of certain active substances such as, for example, steroidal agents or sex hormones to penetrate. It is further intended to avoid as far as possible disadvantages occurring, in particular skin irritation, on use of the known preparations, whether in the form of a transdermal therapeutic system (TTS), of a cream, or of a lotion.

The object is achieved according to the invention by producing a transdermal therapeutic system for application to the skin and/or mucosa, consisting of at least one active substance in the form of a solid dispersion in combination with at least one destructuring agent and/or at least one structuring agent in a common matrix.

The transdermal therapeutic system according to the invention is preferably characterized in that the solid dispersion is a molecular dispersion of the active substance in an inert carrier substance.

The inert carrier substance is selected according to the invention from inert carriers known per se for solid dispersions, such as, for example, sucrose, lactose, succinic acid, polyethylene glycols, polyvinylpyrrolidone, urea, mannitol, mannitose or mixtures thereof.

The destructuring agent is selected according to the invention from the group of carboxamides such as, for example, urea, nicotinamide, succinamide, methylacetamide, ethylacetamide or mixtures thereof.

The relaxation time for the transdermal therapeutic system according to the invention is preferably more than 120 ms, by preference more than 150 ms.

The structuring agent is selected according to the invention from the group of polyols such as, for example, glycerol, ethylene glycol, propylene glycol, from the group of sugar alcohols such as, for example, sorbitol and/or from the group of sugars such as, for example, sucrose or glucose or mixtures thereof.

The relaxation time in this case is preferably less than 119 ms, by preference less than 80 ms.

An appropriate ratio of the components (destructuring agent/structuring agent) has proved particularly advantageous for more efficient transdermal release.

The ratio between destructuring agent and structuring agent according to the invention is from 10:1 to 1:10, the ratio between destructuring agent and structuring agent preferably being from 2:1 to 1:2.

The destructuring agent used is a substance which destroys the structure of water to result in a relaxation time >120 ms, preferably >150 ms. This longer relaxation time is a manifestation of a greater mobility of free water, which is thus available for solution and diffusion processes.

The structuring agent used is a substance which strengthens the structure of water to result in a relaxation time <120 ms, preferably <80 ms. This shorter relaxation time is a manifestation of a reduced mobility of free water, which is thus no longer available for dissolving and diffusion processes.

The stated facts are made clear by an investigation of the $T_2$ relaxation times for selected destructuring agents and structuring agents (Table 2).

TABLE 2

$T_2$ relaxation times for selected destructuring agents and structuring agents in water (concentration: 0.5 mol/l)

| Solute | Type | $T_2$ [ms] | ± SEM [ms] |
| --- | --- | --- | --- |
| — | Water | 129 | 20 |
| Sucrose | Structuring agent | 18.7 | 0.1 |
| Sorbitol | Structuring agent | 119.4 | 14 |
| Urea | Destructuring agent | 145 | 15 |
| Nicotinamide | Destructuring agent | 276 | 24 |

The suitable ratio of the two substances was established in a wide-ranging series of tests on testosterone and other steroid hormones. It emerged from this, surprisingly, that an additive increase in the transdermal flux can be achieved if not only the structure of the water is broken but, at the same time, more active substance is available for dissolving and diffusion through use of a solid dispersion of the active substance in the preparation.

A considerable improvement in the transdermal flux is surprisingly achieved with the transdermal therapeutic system according to the invention. The value for this in the cases investigated is at 1.4 times that for conventional TTS.

If accurate adjustment of the flux is desired for therapeutic requirements, this can be achieved according to the invention by simultaneous use of destructuring agents and structuring agents in an appropriate ratio.

Also provided is a composition according to the invention for transdermal administration, which contains, in an amount of at least more than 10% by weight and less than 90% by weight, a penetration-enhancing agent of the following formula 1

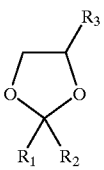

(1)

in which R1 and R2 are identical or different and are selected from the group of C1- to C6-alkyl radicals, in particular the optionally branched, saturated C1- to C4-alkyl radicals, R3 is selected from the group consisting of hydroxy-(C1- to C6-)alkyl radicals, in particular hydroxy-(C1- to C4-)alkyl radicals, and contains at least one active substance or its pharmaceutically acceptable salt and another lipophilic penetration-enhancing agent.

Additionally provided according to the invention is another composition for transdermal administration. This comprises a penetration-enhancing agent of the formula 1 mentioned above, where R1, R2 and R3 are as defined above, at least one active substance or its pharmaceutically acceptable salt and another lipophilic penetration-enhancing agent, excepting oleic acid, whose lipophilicity measured by determining the water absorption capacity is in the region of 0–1.4% by weight, preferably in the region of 0.001–0.330% by weight or in the region of 0.340–1.400% by weight.

The present invention thus relates to a composition for transdermal administration comprising, in an amount of at least more than 10% by weight and less than 90% by weight, a penetration-enhancing agent of the following formula 1

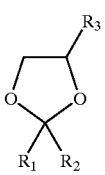

(1)

where R1 and R2 are identical or different and are selected from the group of C1- to C6-alkyl radicals, in particular the optionally branched, saturated C1- to C4-alkyl radicals, R3 is selected from the group consisting of hydroxy-(C1- to C6-)alkyl radicals, in particular hydroxy-(C1- to C4-)alkyl radicals, and at least one pharmaceutical active substance or its pharmaceutically acceptable salt and another lipophilic penetration-enhancing agent.

The present invention also relates to a composition for transdermal administration comprising a penetration-enhancing agent of the following formula 1

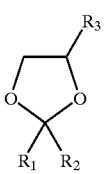

(1)

where R1 and R2 are identical or different and are selected from the group of C1- to C6-alkyl radicals, in particular the optionally branched, saturated C1- to C4-alkyl radicals, R3 is selected from the group consisting of hydroxy-(C1- to C6-)alkyl radicals, in particular hydroxy-(C1- to C4-)alkyl radicals, and at least one pharmaceutical active substance or its pharmaceutically acceptable salt and another lipophilic penetration-enhancing agent, excepting oleic acid, whose lipophilicity measured by determining the water absorption capacity is in the region of 0 to 1.4% by weight, preferably in the region of 0.001 to 0.330% by weight or in the region of 0.340 to 1.400% by weight.

A preferred composition is one where the penetration-enhancing agent of the formula 1 is present in a content of more than 10 to 50% by weight, preferably more than 10 to 25% by weight, most preferably 15 to 25% by weight.

Also preferred is a composition where the penetration-enhancing agent of the formula 1 is Solketal (2,2-dimethyl-4-hydroxymethyl-1,3-dioxolane).

A further preferred composition is one additionally containing a contact adhesive, preferably a contact adhesive based on mixtures containing (co)polymers based on constituents which are selected from the group of C1- to C6-alkyl (meth)acrylates, C1- to C5-hydroxyalkyl (meth)acrylates, in particular containing a contact adhesive based on mixtures containing (co)polymers based on constituents selected from the group consisting of vinyl acetate, 2-ethylhexyl acrylate, 2-hydroxyethyl acrylate, glycidyl methacrylate, butyl acrylate, acrylic acid and methyl acrylate.

Additionally preferred is a composition where the other lipophilic penetration-enhancing agent is selected from the group of saturated hydrocarbons with 10 to 30 C atoms, of the optionally unsaturated fatty alcohols with 10 to 30 C atoms, of the saturated or unsaturated, monobasic or polybasic fatty acids with 8 to 30 C atoms and their esters with optionally unsaturated fatty alcohols with 10 to 30 C atoms, and triacylglycerides with fatty acid residues with 8 to 22 C atoms, preferably with 5 to 12 C atoms.

Particularly preferred in this connection is a composition where the other lipophilic penetration-enhancing agent is selected from the group consisting of dioctylcyclohexane, dodecanol, 2-octyldodecanol, 2-hexyldodecanol, oleyl alcohol, lauric acid, oleic acid, palmitic acid, dioctyl ether, isopropyl myristate, hexyl laurate, cetearyl isononanoate, capric acid, (C1- to C20-)alkyl caprates, (C1- to C20-)alkyl oleates, in particular decyl oleate, oleyl oleate, (C1- to C20-)alkyl docosenoates).

A very particularly preferred composition in this connection is one where the other lipophilic penetration-enhancing agent is ethyl oleate.

A further preferred composition is one where the other lipophilic penetration-enhancing agent is present in a relative amount of at least 2% by weight, preferably between 5 and 15% by weight.

A preferred composition is also one where another hydrophilic penetration-enhancing agent which preferably has a solubility of at least 5% by weight in water is present.

A particularly preferred composition in this connection is one where the other hydrophilic penetration-enhancing agent is selected from the group consisting of amides, polyethylene glycols, glycols, pyrrolidones, polymers of pyrrolidone derivatives, in particular nicotinamide or urea.

A very particularly preferred composition is one where the other hydrophilic penetration-enhancing agent is present in a relative amount of from 1 to 10% by weight, preferably 2 to 5% by weight.

A further preferred composition is one where the active substance is a lipophilic active substance, in particular a steroidal agent.

A particularly preferred composition in this connection is one where the steroidal agent is a steroid hormone, in particular selected from the group consisting of corticosteroids, sex hormones, preferably oestrogens, gestagens, androgens, in particular from the group consisting of testosterone, estradiol and its derivatives, particularly preferably testosterone, estradiol, ethinylestradiol and norethisterone acetate.

An additionally preferred composition is one where the composition contains the active substance in at least saturated solution, preferably in supersaturated solution.

The active substances present in the transdermal therapeutic system according to the invention can be selected virtually as desired. Preferred active substances according to the invention are selected from hormones, immunomodulators, immunosuppressants, antibiotics, cytostatics, diuretics, gastrointestinal agents, cardiovascular agents and neuropharmaceuticals or mixtures thereof.

Hormones are particularly preferred, especially sex hormones such as, for example, testosterone, estradiol, estriol, norethisterone, dienogest or mixtures thereof.

The transdermal therapeutic systems according to the invention can be produced by simple methods. These methods are essentially based on well-known pharmaceutical technologies. The method avoids in principle all elaborate precision fabrication or special coating techniques. The method affords medicinal forms from which there is improved penetration of hydrophilic medicinal substances through the skin.

The active substances are moreover used according to the invention in the form of solid dispersions. Corresponding dispersions can be prepared, for example, as disclosed in DE-A 44 02 462.

The present invention furthermore relates to means for transdermal administration comprising the composition according to the invention described above.

Particularly preferred in this connection is the means comprising an emulsion, ointment, cream, lotion or transdermal therapeutic system (TTS).

A particularly preferred TTS in this connection is one with an optionally detachable protective layer (1), at least one contact adhesive matrix layer, in particular a contact adhesive-containing primer layer (2), and a contact adhesive-containing cutaneous layer (3), another intermediate layer (4) and an optionally active substance- and/or water vapour-impermeable backing layer (5).

A particularly preferred TTS is one where the primer layer (2) and the cutaneous layer (3) project beyond the intermediate layer (4) on all sides.

Also preferred in this connection is a TTS where the composition is present where appropriate distributed in three compartments, namely the contact adhesive-containing primer layer (2), the contact adhesive-containing cutaneous layer (3) and the other intermediate layer (4).

The matrix of the transdermal therapeutic system is according to the invention a sheet-like adhesive material, a plaster, a patch, a gel, an ointment, a cream, an emulsion, an embrocation, a paint or an impregnated fabric.

The present invention thus relates not only to the known sheet-like adhesive materials (plasters, patches) but also to gels, ointments, creams, emulsions, embrocations, paints, impregnated.fabric and similar administration devices of transdermal therapeutic systems as long as they adhere to the skin or mucosa target organ.

The invention further relates to a method for producing the TTS according to the invention described above, comprising the steps of producing a first laminate by a first mixture containing the at least one active substance and an optionally cross-linkable contact adhesive being produced and applied to a protective layer (1) carrier material, producing a second laminate by applying the first mixture to a backing layer (5) carrier material, a disc being punched out of another carrier material, preferably a nonwoven, and being applied to the first laminate, and a second mixture containing the penetration-enhancing agent of formula 1 and the other lipophilic penetration-enhancing agent being applied to the other carrier material, the second laminate being laminated thereon and single TTS being produced therefrom.

The production of the TTS is otherwise based on the pharmaceutical technology known in principle for these systems and thus can be carried out in the pharmaceutical production facilities customary for this purpose without special measures.

The invention finally relates to a product produced by this method for use in replacement therapy, in particular hormone replacement therapy.

A preferred product in this connection is one for use for hypogonadism, anaemia, congenital angioneurotic oedema, impotence, infertility or contraception.

Figure 1:
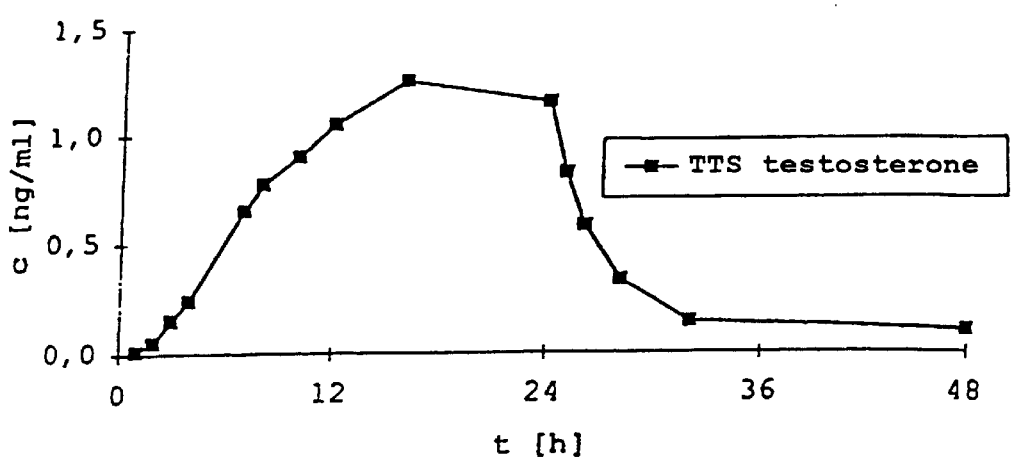
FIG. 1 shows the average serum concentrations of testosterone over a period of 48 hours in the test subjects (n=8). The serum concentrations are in the range from 0.01 ng/ml after 1 hour to 1.25 ng/ml after 16 hours.

The invention is illustrated in detail by the following examples.

INVESTIGATION METHOD 1

The transdermal permeation of the appropriate medicinal substances through excised cow udder skin (thickness 1.2 mm) was investigated in a modified FRANZ cell (Hansen-Research). At the start of the test, the vehicles used were introduced into the donor compartment of the cell, and the weight of active substance m permeated over a period of 56 h was quantified by complete removal and replacement of the acceptor compartment after t=8, 24, 32, 48 and 56 hours by UV or fluorescence spectroscopy detection and HPLC separation. The m/t profiles in the time segment 24 h≦t≦56 h were linearized to calculate the in vitro flux J from the gradient of the regression lines.

EXAMPLE 1

0.5% testosterone hydrogel

The following hydrogel was used:

| | |
|---|---|
| Testosterone | 0.500 g |
| Carbopol ® 934 | 0.500 g |
| Triethanolamine | 0.500 g |
| Ethanol 96% | 46.875 g |
| Aqua purificata | ad 100.000 g |

The destructuring/structuring agents listed in Table 3 were added in appropriate concentration to the hydrogel, and the water content was reduced by the appropriate weight.

The transdermal in vitro flux values J of the hydrogels, the standard deviation S and the corresponding enhancement factors in the presence of a destructuring/structuring agent are shown in Table 3.

TABLE 3

Flux J and enhancement factor $F_E$ of the testosterone hydrogels with and without addition of destructuring/structuring agents

| Destructuring agent | Structuring agent | Concentration | Flux J ± S [$\mu$g/cm$^2$*h] | $F_E$ |
|---|---|---|---|---|
| / | / | / | 3.1 ± 1.1 | |
| Nicotinamide | / | 0.5 mol/kg | 5.5 ± 1.2 | 1.75 |
| Urea | / | 0.5 mol/kg | 6.9 ± 2.3 | 2.22 |
| / | Lactose | 45 g/kg | 3.7 ± 0.7 | 1.19 |
| / | Lactose (solid dispersion) | 45 g/kg | 7.4 ± 0.7 | 2.39 |
| Nicotinamide | Lactose (solid dispersion) | 0.5 mol/kg/ 45 g/kg | 11.8 ± 2.4 | 3.8 |

The flux J is found to be between 3.1±1.1 $\mu$g/cm$^2$*h and 11.8±2.4 $\mu$g/cm$^2$*h. The enhancement factors on addition of destructuring/structuring agents are between 1.75 and 3.8. It was thus possible to show that the in vitro flux of active substances can be increased by adding destructuring agents and/or structuring agents in solid dispersions with the active substance. A combination of the two "enhancers" increases the flux additively.

EXAMPLE 2

4% estriol cream

The following cream was used:

| | |
|---|---|
| Estriol | 4.000 g |
| Preservative | 0.025 g |
| Propylene glycol | 2.000 g |
| Silicone oil | 2.000 g |
| Glycerol monostearate, self-emulsifying | 5.000 g |
| Triglycerides, medium chain length | 5.000 g |
| Lipid phase | 35.200 g |
| Purified water | 46.775 g |

The destructuring/structuring agents listed in Table 4 were added in appropriate concentration to the hydrogel, and the water content was reduced by the appropriate weight.

The transdermal in vitro flux values J of the creams, the standard deviation S and the corresponding enhancement factors $F_E$ in the absence of a destructuring/structuring agent are shown in Table 4.

TABLE 4

Flux J and enhancement factor $F_E$ of the estriol cream with and without addition of destructuring/structuring agents

| Destructuring agent | Structuring agent | Concentration | Flux J ± S [µg/cm²*h] | $F_E$ |
|---|---|---|---|---|
| / | / | / | 0.184 + 0.023 | |
| Nicotinamide | / | 1 mol/l | 0.508 ± 0.060 | 2.76 |

The flux was found to be between 0.184±0.023 µg/cm²*h and 0.508±0.060 µg/cm²*h. The enhancement factor on the addition of nicotinamide is 2.76. It was thus possible to show that the in vitro flux of active substances can be increased by adding destructuring agents.

EXAMPLE 3

0.5% dienogest hydrogel
The following hydrogel was used:

| | |
|---|---|
| Dienogest | 0.500 g |
| Carbopol ® 934 | 0.500 g |
| Triethanolamine | 0.500 g |
| Ethanol 96% | 46.875 g |
| Aqua purificata | ad 100.000 g |

The destructuring/structuring agents listed in Table 5 were added in appropriate concentration to the hydrogel, and the water content was reduced by the appropriate weight.

The transdermal in vitro flux values J of the hydrogels, the standard deviation S and the corresponding enhancement factors in the presence of a destructuring/structuring agent are shown in Table 5.

TABLE 5

Flux J and enhancement factor $F_E$ of the dienogest hydrogels with and without addition of destructuring/structuring agents

| Destructuring agent | Structuring agent | Concentration | Flux J ± S [µg/cm²*h] | $F_E$ |
|---|---|---|---|---|
| / | / | / | 1.38 + 0.27 | |
| Nicotinamide | lactose (solid dispersion) | 0.5 mol/kg 45 g/kg | 1.97 ± 0.26 | 1.43 |

The flux J was found to be between 1.38±0.27 g/cm²*h and 1.97±0.26 µg/cm²*h. The enhancement factors on addition of destructuring/structuring agents are 1.43. It was thus possible to show that the in vitro flux of active substances can be increased by adding destructuring agents and/or structuring agents in solid dispersions with the active substance.

INVESTIGATIVE METHOD 2
Study Design

An open randomized three-arm cross-over study was carried out with one arm being the testosterone TTS. This TTS is intended to release 2.5 mg of testosterone in a controlled manner over 24 hours. The test subjects selected were 9 postmenopausal or menopausal women from 20 to 65 years of age.

The testosterone TTS was applied at time $t_0$ to the forearm and removed after 24 hours. The serum was taken at defined times and analysed for the testosterone concentration by RIA. The last sample was taken 24 hours after removal of the TTS.

EXAMPLE 4

The testosterone TTS investigated had the composition shown in Table 6.

TABLE 6

Composition of the testosterone TTS

| Raw material | Content/TTS | % in the matrix |
|---|---|---|
| Testosterone | 8.4 mg | 3.00 |
| Nicotinamide | 14.0 mg | 5.00 |
| Matrix | 257.6 mg | 92.00 |
| Backing layer | 35.0 cm² | |
| Release liner | 46.2 cm² | |

The average testosterone serum concentrations with the testosterone TTS in the pilot study are compiled in Table 7.

TABLE 7

Testosterone serum concentrations c with the testosterone TTS as a function of the time t

| t [h] | 1 | 2 | 3 | 4 | 5 | 7 | 8 | 10 |
|---|---|---|---|---|---|---|---|---|
| c [ng/ml] | 0.01 | 0.05 | 0.15 | 0.24 | 0.62 | 0.65 | 0.77 | 0.90 |
| t [h] | 12 | 16 | 24 | 25 | 26 | 28 | 32 | 48 |
| c [ng/ml] | 1.05 | 1.25 | 1.15 | 0.82 | 0.58 | 0.33 | 0.14 | 0.10 |

FIG. 1 shows the average serum concentrations of testosterone over a period of 48 hours in the test subjects (n=8). The serum concentrations are in the range from 0.01 ng/ml after 1 hour to 1.25 ng/ml after 16 hours.

After a short lag time of about 2 hours, there is seen to be a marked rise in the serum concentrations, which remains constant in the region above 1 ng/ml over 12 hours. 24 hours after application of the TTS, the serum level plot declines relatively abruptly. This means that after about 24 hours most of the testosterone has diffused out of the TTS and permeated through the skin.

INVESTIGATIVE METHOD 3

Study Design

An open randomized three-arm cross-over study with "single dose" administration was carried out. The three arms were three estriol creams having the same base part differing in the dose of active substance. The intention was to establish the bioavailability of estriol after transdermal administration. The test subjects selected were 9 postmenopausal women. The appropriate estriol creams were applied at time $t_0$ to the forearm. The serum was taken at defined times in a period up to 24 hours and analysed for the estriol concentration by RIA. The last sample was taken 24 hours after application of the creams.

EXAMPLE 5

Estriol Creams

The composition of the creams investigated is compiled in Table 8.

TABLE 8

Composition of estriol creams 1, 3 and 10

| Active substances and auxiliaries | Estriol 1 | Estriol 3 | Estriol 10 |
|---|---|---|---|
| Estriol | 1.000 g | 3.000 g | 10.000 g |
| Preservatives | 0.025 g | 0.024 g | 0.022 g |
| Propylene glycol | 1.980 g | 1.940 g | 1.800 g |
| Silicone oil | 1.980 g | 1.940 g | 1.800 g |
| Glycerol monostearate, self-emulsifying | 4.950 g | 4.850 g | 4.500 g |
| Triglycerides, medium chain length | 4.950 g | 4.850 g | 4.500 g |
| Lipid phase | 34.848 g | 34.144 g | 31.680 g |
| Nicotinamide | 6.039 g | 5.917 g | 5.490 g |
| Purified water | 44.228 g | 43.335 g | 40.208 g |

Figure 2:
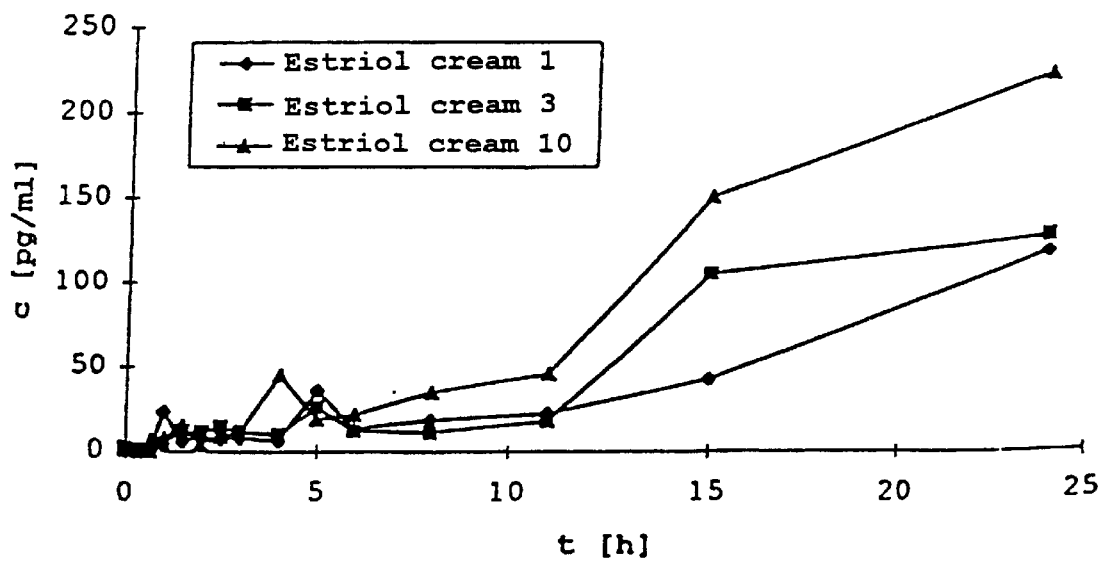
FIG. 2 shows the average estradiol concentrations in the serum of the test subjects (n=8) over a period of 24 hours. The serum concentrations are in the range from 1.09 pg/ml after 0 hours up to 222.04 pg/ml after 24 hours (estradiol cream 10 in each case).

FIG. 2 shows the average estriol concentrations in the serum of the test subjects (n=8) over a period of 24 hours. The serum concentrations are in the range from 1.09 pg/ml after 0 hours up to 222.04 pg/ml after 24 hours (estriol cream 10 in each case).

After a lag time of about 10–12 hours there is seen to be a marked rise in the serum concentrations. They are highest with estriol cream 10 and lowest with estriol cream 1. There is an evident dependence of the serum concentrations on the concentration and dose. Since the serum concentrations continue to rise up to 24 hours after application with all three creams, a further rise in the serum concentrations is to be expected.

INVESTIGATIVE METHOD 4

To examine the principle of action of the destructuring agents, NMR experiments were carried out in a Bruker Biospec 47/40 (Fraunhofer-Institut für Biomedizinische Technik, D-St. Ingbert). The field strength was 4.7 T. For reliability, three mutually adjacent coronal slices were recorded simultaneously for the distal phalanx of the subject's middle finger in one experiment in each case (repetition time 1.5 s). 8 echo images were recorded with a time interval of 8 ms for the slice (Hermite pulses, duration 1 ms) to result in 24 images. The thickness of the selected slices was 2 mm. 256*256 pixels covering a field of 3 cm were recorded for each image. This ensured a resolution of 120 µm in the plane of the image. The TOMIKON software was used for analysis.

EXAMPLE 6

Hydrogel with 0.5 mol/kg nicotinamide

A gel with the inventive principle (cf. Example 1) was compared with a gel without additions by application to the subjects (active substance-free gels were used for reasons connected with medicinal product legislation).

The investigation showed
1. from the proton spin density an effect on the water (probably in region B) by the principle according to the invention,
2. from the $T_2$ relaxation times a distinct effect on the outer layers of skin by the principle according to the invention.

A $T_2$ value of 46.4 ms was found in this in vitro study for an ethanolic hydrogel without added nicotinamide. The addition of 1 M nicotinamide led to a $T_2$ value of 61.2 ms, whereas demonstration of the gel with added nicotinamide using the HSP technique (solid dispersion of active substance and lactose) led to a shortening of the $T_2$ relaxation time of 34.0 ms.

Summarizing, the result of the investigations can be summarized as follows:

A destructuring agent makes free water available for dissolving and diffusion. It is moreover possible to adjust the extent of this process by the nature and/or concentration of the destructuring agent and/or by admixing a structuring agent very accurately to the requirements in each case.

The active substance can, if it is in the form of a solid dispersion, rapidly dissolve and diffuse in the free water.

INVESTIGATIVE METHOD 5

Study Design

An open randomized four-arm cross-over study was carried out with one arm being a testosterone TTS as in Example 7. This TTS is intended to release 3.5 mg of testosterone in a controlled manner over 24 hours. The test subjects selected were 8 post- or menopausal women from 20 to 65 years of age.

The testosterone TTS was applied at time $t_0$ to the forearm and removed after 24 hours. Blood was taken from the women at defined times, and the serum testosterone concentration was analysed by RIA. The last blood sample was taken 10 hours after removal of the TTS.

EXAMPLE 7

The investigated testosterone TTS had the composition shown in Table 9.

TABLE 9

Composition of the testosterone TTS

| Raw material | Content/TTS | % in the matrix |
|---|---|---|
| Testosterone | 21.0 mg | 3.50 |
| Nicotinamide | 21.0 mg | 3.50 |
| Matrix components | 556.32 mg | 93.00 |
| Backing layer | 35.0 cm$^2$ | |
| Release liner | 46.2 cm$^2$ | |

The average serum testosterone concentrations the testosterone TTS are compiled in Table 10.

TABLE 10

Serum testosterone concentrations c with the testosterone TTS as a function of time t

| t [h] | 0 | 1.5 | 3 | 5 | 7 | 9 | 12 | 16 |
|---|---|---|---|---|---|---|---|---|
| c [ng/ml] | 0 | 0.04 | 0.40 | 0.78 | 1.40 | 1.57 | 1.88 | 2.20 |
| t [h] | 24 | 25 | 26 | 27 | 28 | 30 | 32 | 34 |
| c [ng/ml] | 2.00 | 1.29 | 1.21 | 0.98 | 0.86 | 0.76 | 0.43 | 0.24 |

Figure 3:
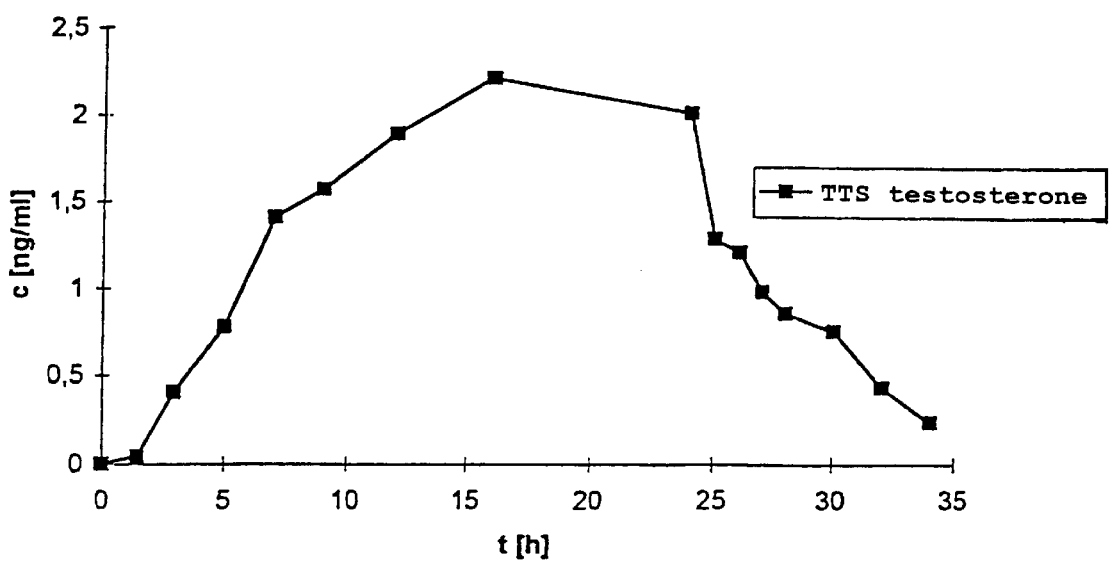
FIG. 3 shows the average serum concentrations (n=8) of testosterone over a period of 34 hours. The serum concentrations are in the range from 0.04 ng/ml after 1.5 hours to 2.20 ng/ml after 16 hours.

FIG. 3 shows the average serum concentrations (n=8) of testosterone over a period of 34 hours. The serum concentrations are in the range from 0.04 ng/ml after 1.5 hours to 2.20 ng/ml after 16 hours. After a short lag time of about 2 hours, there is a marked increase in the serum concentrations, which remains in the region above 1 ng/ml over 20 hours. 24 hours after application of the TTS, the serum level plot shows a continuous decline simultaneously with the removal of the TTS.

What is claimed is:

1. Process for producing a transdermal therapeutic system comprising the steps of producing a first laminate containing a mixture of at least one active substance and an optionally cross-linkable contact adhesive and applying the mixture to a protective layer carrier material; producing a second laminate by applying the first mixture to a backing layer carrier material; punching out a disc of a second carrier material which is then applied to the first laminate; producing a second mixture containing a composition comprising a penetration-enhancing agent in an amount of at least more than 10% by weight and less than 90% by weight, at least one pharmaceutically active substance or its pharmaceutically acceptable salt, and another lipophilic penetration-enhancing agent; applying this second mixture onto said disc of the second carrier material; and laminating the first and second laminates together and producing single transdermal therapeutic systems therefrom.

2. Process for producing a transdermal therapeutic system comprising the steps of producing a first laminate containing a mixture of at least one active substance and an optionally cross-linkable contact adhesive and applying the mixture to a protective layer carrier material; producing a second laminate by applying the first mixture to a backing layer carrier material; punching out a disc of a second carrier material which is then applied to the first laminate; producing a second mixture containing a composition comprising a penetration-enhancing agent, at least one pharmaceutically active substance or its pharmaceutically acceptable salt, and another lipophilic penetration-enhancing agent whose lipophilicity measured by determining its water absorption capacity is between 0 and 1.4% by weight, with the proviso that the lipophilic penetration-enhancing agent is not oleic acid; applying this second mixture onto said disc of the second carrier material; and laminating the first and second laminates together and producing single transdermal therapeutic systems therefrom.

3. The method of claim 1 wherein the penetration-enhancing agent comprises formula (1)

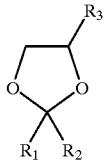

(1)

wherein $R_1$ and $R_2$ are identical or different and are selected from the groups of $C_1$- to $C_6$-alkyl radicals, and $R_3$ is selected from the group consisting of hydroxy-($C_1$- to $C_6$-) alkyl radicals.

4. The method of claim 2 wherein the penetration-enhancing agent comprises formula (1)

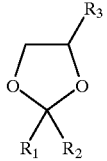

(1)

wherein $R_1$ and $R_2$ are identical or different and are selected from the groups of $C_1$- to $C_6$-alkyl radicals, and $R_3$ is selected from the group consisting of hydroxy-($C_1$- to $C_6$-) alkyl radicals.

* * * * *